(12) United States Patent
Negi et al.

(10) Patent No.: US 7,858,809 B2
(45) Date of Patent: Dec. 28, 2010

(54) PROCESS FOR PRODUCTION OF PYRAZOLE-FUSED RING DERIVATIVES

(75) Inventors: Shigeto Negi, Kashima-gun (JP);
Toshikazu Shimizu, Kashima-gun (JP);
Hiroshi Kuroda, Kashima-gun (JP);
Naoyuki Shimomura, Tsukuba (JP);
Manabu Sasho, Bunkyo-ku (JP);
Yorihisa Hoshino, Tsukuba (JP);
Manabu Kuboto, Kashima-gun (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 922 days.

(21) Appl. No.: 11/578,134

(22) PCT Filed: Apr. 8, 2005

(86) PCT No.: PCT/JP2005/006928

§ 371 (c)(1),
(2), (4) Date: Oct. 10, 2006

(87) PCT Pub. No.: WO2005/100354

PCT Pub. Date: Oct. 27, 2005

(65) Prior Publication Data

US 2007/0191613 A1 Aug. 16, 2007

(30) Foreign Application Priority Data

Apr. 12, 2004 (JP) ............................. 2004-116611

(51) Int. Cl.
C07D 231/54 (2006.01)
(52) U.S. Cl. .................................. 548/360.1
(58) Field of Classification Search ................ 546/121; 548/360.1
See application file for complete search history.

(56) References Cited

U.S. PATENT DOCUMENTS

| | | | | |
|---|---|---|---|---|
| 5,234,818 | A * | 8/1993 | Zimmermann et al. | 435/28 |
| 7,176,216 | B2 * | 2/2007 | Hibi et al. | 514/300 |
| 7,323,569 | B2 * | 1/2008 | Hibi et al. | 546/121 |
| 2003/0065187 | A1 | 4/2003 | Buchwald et al. | |
| 2004/0019216 | A1 | 1/2004 | Buchwald et al. | |
| 2004/0122039 | A1 * | 6/2004 | Hibi et al. | 514/300 |
| 2004/0224974 | A1 | 11/2004 | Hibi et al. | |

FOREIGN PATENT DOCUMENTS

| | | | |
|---|---|---|---|
| WO | WO-00/59907 | A2 | 10/2000 |
| WO | WO-00/59908 | A | 10/2000 |
| WO | WO-02/85838 | A1 | 10/2002 |
| WO | WO-02/088121 | A1 | 11/2002 |
| WO | WO 02088121 | A1 * | 11/2002 |
| WO | WO-03/078435 | A1 | 9/2003 |
| WO | WO-2004/037822 | A1 | 5/2004 |

OTHER PUBLICATIONS

Armarego et al. Purification of Laboratory Chemicals, 4th edition, published 1996, p. 51.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. Advanced Drug Delivery Reviews, 48 (2001), pp. 3-26.*
B. Rodriquez-Spong et al. Advanced Drug Delivery Reviews, 2004, 56, pp. 241-274.*
Artis Klapars et al., J. Am. Chem. Soc. 2002, 124, pp. 7421-7428.

* cited by examiner

*Primary Examiner*—Rebecca L Anderson
*Assistant Examiner*—Matthew P Coughlin
(74) *Attorney, Agent, or Firm*—Birch, Stewart, Kolasch & Birch, LLP

(57) ABSTRACT

Intermediates useful for the synthesis of pyrazole-fused ring derivatives, such as 7-phenylpyrazolo [1,5-a]pyridine derivatives, and method for producing the same. Method for producing compound represented by the general formula (II), wherein $Z^1$ and $Z^2$ each independently represents a methine group or a nitrogen atom; $R^1$ represents an ethyl group or the like; $R^5$ represents a hydrogen atom or the like; $R^2$ and $R^3$ each independently represents a $C_{1-6}$ alkyl group or the like, salts thereof, or solvates of both, comprising the step of: reacting a compound represented by the general formula (I), wherein $Z^1$, $Z^2$, $R^5$, $R^1$, $R^2$ and $R^3$ each has the same definition as described above, with an organometallic reagent; and then reacting the resulting product with pentafluoroiodobenzene.

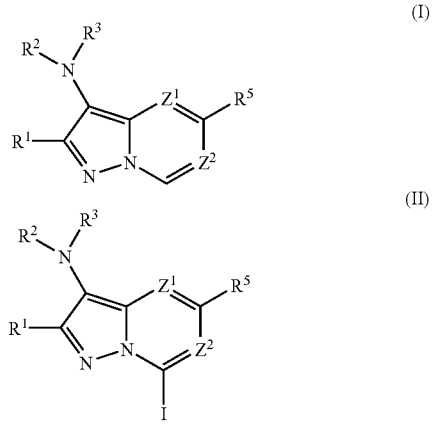

5 Claims, No Drawings

PROCESS FOR PRODUCTION OF PYRAZOLE-FUSED RING DERIVATIVES

TECHNICAL FIELD

The present invention relates to a method for producing pyrazole-fused ring derivatives (such as pyrazolo[1,5-a]pyridine derivatives and the like) useful as synthesis intermediates of pyrazole-fused ring derivatives (such as 7-phenylpyrazolo[1,5-a]pyridine derivatives and the like) useful for prevention or treatment of depression, anxiety and the like as acorticotrophin-releasing-factor (CRF) receptor antagonist, and pyrazole-fused ring derivatives (such as 7-iodopyrazolo[1,5-a]pyridine derivatives and the like) or salts thereof, or solvates thereof.

BACKGROUND ART

There are reports on (1)-7-phenylpyrazolo[1,5-a]pyridine derivatives and a method for producing the same (see Patent Documents 1 and 2), (2) 7-phenylpyrazolopyrimidine derivatives and a method for producing the same (see Patent Document 3) and (3) 7-phenylpyrazolotriazine derivatives and a method for producing the same (see Patent Document 4), which have a CRF receptor antagonistic action and expected as a therapeutic agent for depression, anxiety and the like.

Regarding a step of a halogenating reaction and a step of an amino group introducing reaction in the methods for producing pyrazole-fused ring derivatives (7-phenylpyrazolo[1,5-a]pyridine derivatives and the like) described in the documents, the following points are mentioned as problems in the case of use for industrial production.

(1) In the step of a halogenating reaction, purification by column chromatography is used after reaction.

(2) In the step of a halogenating reaction, 1,2-diiodoethane which is not so suitable for industrial production is used as a halogenating reagent.

(3) Regarding the step of a halogenating reaction, there is a lot of examples showing a yield of 60 to 70% in an iodination reaction of a pyrazolo[1,5-a]pyridine derivative using 1,2-diiodoethane, revealing unsatisfactory yields. (see Patent Document 2)

(4) In the step of introducing an amino group into a pyrazole-fused ring derivative (pyrazolo[1,5-a]pyridine ring and the like), a reduction reaction-alkylation reaction after a nitration reaction is used or a Crutius reaction from a carboxylic acid derivative is used; however, these reactions show poor yields and reaction steps thereof are long. Further, a 3-aminopyrazopyridine compound which is an intermediate in these reactions is unstable, and is not suitable as an intermediate in an industrial synthesis method.

Taking the above-described points into consideration, the production methods described in the documents are not satisfactory as an industrial production method.

A compound represented by following formula, which is a 7-iodopyrazolo[1,5-a]pyridine derivative or a salt thereof, or a solvate thereof, is a novel compound and is not known until now.

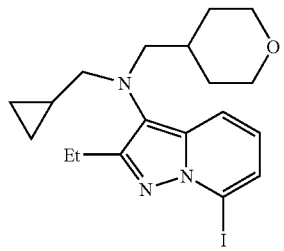

[Regarding Iodination Reaction]

Although pentafluoroiodobenzene is a known compound, there is no example using pentafluoroiodobenzene as a reagent in an iodination reaction. Regarding an iodination reaction step of a pyrazole-fused ring derivative (pyrazolo[1,5-a]pyridine derivative and the like), it is reported that n-butyllithium and 1,2-diiodoethane as described above (see Patent Documents 1 and 2) were used.

[Regarding an Amidation Reaction by a Coupling Reaction to a Bi-cyclic Heteroaromatic Compound]

Regarding a reaction for amidating an aryl halide using a copper catalyst, Buchwald et al. made a report (see Non-Patent Document 1). However, there is known no amidation reaction by a coupling reaction to a bi-cyclic heteroaromatic compound such as pyrazolo[1,5-a]pyridine and the like.

Patent Document 1: International Publication No. 02/088121, pamphlet.
Patent Document 2: International Publication No. 03/078435, pamphlet.
Patent Document 3: International Publication No. 00/59908, pamphlet.
Patent Document 4: International Publication No. 00/59907, pamphlet.
Non-Patent Document 1: J. Am. Chem. Soc., 7421-7428, 124, 2002.

DISCLOSURE OF INVENTION

Problem to be Solved by Invention

An object of the present invention is related to (1) a method for producing a pyrazole-fused ring derivative (pyrazolo[1,5-a]pyridine derivative and the like), and (2) a pyrazole-fused ring derivative (7-iodopyrazolo[1,5-a]pyridine derivative and the like) or a salt thereof, or a solvate thereof, which are useful as a synthesis intermediate of a pyrazole-fused ring derivative (the above-described 7-phenylpyrazolo[1,5-a]pyridine derivative and the like).

Means for Solving the Problem

Taking the above-described things into consideration, the present inventors have intensively investigated, energetically studied, and resultantly have found (1) a method for producing a pyrazole-fused ring derivative (pyrazolo[1,5-a]pyridine derivative and the like), and (2) a pyrazole-fused ring derivative (7-iodopyrazolo[1,5-a]pyridine derivative and the like) or a salt thereof or a solvate thereof, which are useful as a synthesis intermediate of a pyrazole-fused ring derivative (the above-described 7-phenylpyrazolo[1,5-a]pyridine derivative and the like). The present invention relates to the following inventions:

[1] A method for preparing a compound (II) represented by following formula:

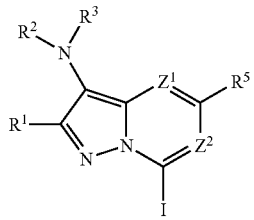

(wherein $Z^1$ and $Z^2$ each independently represents a methine group or a nitrogen atom;

$R^5$ represents a hydrogen atom or a $C_{1-6}$ alkyl group;

$R^1$ represents a group represented by the formula —$R^{10}$—$R^{11}$ (wherein $R^{10}$ represents a single bond, an oxygen atom or a sulfur atom; $R^{11}$ represents a methyl group or an ethyl group) or a methoxymethyl group;

$R^2$ and $R^3$ each independently represents a hydrogen atom, a t-butoxycarbonyl group or a group represented by the formula —$X^{21}$-$X^{31}$ (wherein $X^{21}$ represents a methylene group or a carbonyl group; $X^{31}$ represents a $C_{1-6}$ alkyl group, a $C_{3-8}$ cycloalkyl group, a tetrahydropyran-yl group or a tetrahydrofuran-yl group)) or a salt thereof, or a solvate thereof: comprising the steps of:

reacting a compound (I) represented by following formula:

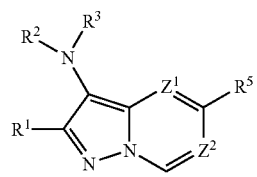

(wherein $Z^1$, $Z^2$, $R^1$, $R^2$, $R^3$ and $R^5$ have the same definitions as described above for $Z^1$, $Z^2$, $R^1$, $R^2$, $R^3$ and $R^5$, respectively) with an organometallic reagent, and thereafter reacting the resulting product with pentafluoroiodobenzene, to produce the compound (II) or a salt thereof, or a solvate thereof.

[2] The production method according to the above item [1], wherein the organometallic reagent is n-butyllithium, t-butyllithium, sec-butyllithium, phenyllithium, lithiumdiisopropylamide, n-butylmagnesiumbromide or isopropylmagnesiumbromide.

[3] The production method according to the above item [1] or [2], wherein iodine is added after reacting pentafluoroiodobenzene.

[3.1] The production method according to any one of the above items [2], [3] and [4], wherein the reaction of a compound represented by the formula (I) with the organometallic reagent is carried out at −40° C. or lower (more preferably −40 to −75° C.)

[3.2] The production method according to any one of the above items [1], [2], [3] and [3.1], wherein the organometallic reagent is used in an amount of 1 to 2-fold mol (more preferably 1.4 to 1.6-fold mol) based on the amount of the compound represented by the formula (I).

[3.3] The production method according to any one of the above items [1], [2], [3], [3.1] and [3.2], wherein the reaction of the compound represented by the formula (I) with pentafluoroiodobenzene is carried out at −30° C. or lower (more preferably −30 to −75° C.).

[3.4] The production method according to any one of the above items [1], [2], [3], [3.1], [3.2] and [3.3], wherein pentafluoroiodobenzene is used in an amount of 1 to 2-fold mol (more preferably 1.4 to 1.6-fold mol) based on the amount of the compound represented by the formula (I).

[3.5] The production method according to any one of the above items [1], [2], [3], [3.1], [3.2], [3.3] and [3.4], wherein iodine is used in an amount of 1 to 2-fold mol (more preferably 1.4 to 1.6-fold mol) based on the amount of pentafluoroiodobenzene.

[4] A method for preparing a compound represented by following formula:

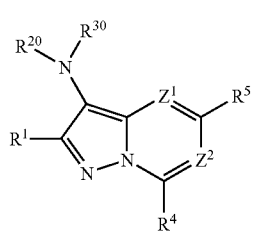

(wherein $R^{20}$ and $R^{30}$ each independently represents a hydrogen atom or a group represented by the formula —$X^{22}$—$X^{32}$ (wherein, $X^{22}$ represents a methylene group or a carbonyl group; and $X^{32}$ represents a $C_{1-6}$ alkyl group, a $C_{3-8}$ cycloalkyl group, a tetrahydropyran-yl group or a tetrahydrofuran-yl group);

$R^4$ represents a hydrogen atom, a chlorine atom, a bromine atom, an iodine atom or a group represented by

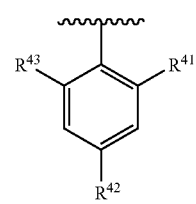

(wherein $R^{41}$, $R^{42}$ and $R^{43}$ each independently represents (1) a hydrogen atom, (2) a halogen atom, (3) a $C_{1-6}$ alkoxy group optionally having 1 to 2 groups selected from the group consisting of a fluorine atom, a chlorine atom, a bromine atom, a cyano group, $C_{1-6}$ alkoxy groups, a pyrrolidinyl group, a piperazinyl group, a piperidyl group, a morpholinyl group, $C_{3-8}$ cycloalkyl groups, a tetrahydropyran-yl group and a tetrahydrofuran-yl group, or (4) a $C_{1-6}$ alkyl group optionally having 1 to 2 groups selected from the group consisting of a fluorine atom, a chlorine atom, a bromine atom, a cyano group, $C_{1-6}$ alkoxy groups, a pyrrolidinyl group, a piperazinyl group, a piperidyl group, a morpholinyl group, $C_{3-8}$ cycloalkyl groups, a tetrahydropyran-yl group and a tetrahydrofuran-yl group); and $Z^1$, $Z^2$, $R^1$ and $R^5$ have the same definitions as described in the above item [1] for $Z^1$, $Z^2$, $R^1$ and $R^5$) or a salt thereof, comprising the step of:

reacting a compound represented by following formula:

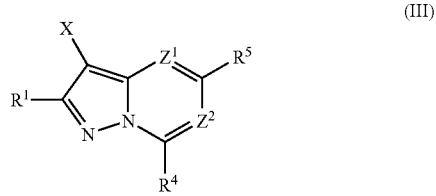

(wherein $Z^1$, $Z^2$, $R^1$, $R^4$ and $R^5$ have the same definitions as described above for $Z^1$, $Z^2$, $R^1$, $R^4$ and $R^5$, respectively; X represents a releasing group) with a compound represented by following formula:

(wherein $R^{20}$ and $R^{30}$ have the same definitions as described above) in the presence of a metal catalyst (such as copper catalysts, palladium catalysts or the like), a phosphate and an amine compound, to produce the above-described compound or the salt thereof.

[5] The production method according to the above item [4], wherein the metal catalyst is copper (I) iodide, copper (II) iodide, copper (I) bromide, copper (II) bromide, copper (I) chloride, copper (II) chloride, copper (I) acetate, copper (II) acetate or copper oxide.

[6] The production method according to the above item [4] or [5], wherein the phosphate is tripotassium phosphate, dipotassium hydrogen phosphate, trisodium phosphate, disodium hydrogen phosphate, trilithium phosphate, dilithium hydrogen phosphate or magnesium phosphate or a hydrate thereof.

[7] The production method according to any one of the above items [4] to [6], wherein the amine compound is 1,2-cyclohexanediamine, N,N'-dimethylethylenediamine, tetramethylethylenediamine or phenanthroline.

[7.1] The production method according to any one of the above items [4], [5], [6] and [7], wherein the reaction of the compound represented by the formula (III) with the compound represented by the formula (IV) is carried out at 50 to 200° C. (more preferably 90 to 150° C.).

[7.2] The production method according to any one of the above items [4], [5], [6], [7] and [7.1], wherein the copper catalyst is used in an amount of 0.001 to 1,0-fold mol (more preferably 0.18 to 0.22-fold mol) based on the amount of the compound represented by the formula (III).

[7.3] The production method according to any one of the above items [4], [5], [6], [7], [7.1] and [7.2], wherein the compound represented by the formula (IV) is used in an amount of 1.0 to 3.0-fold mol (more preferably 1.0 to 1.5-fold mol) based on the amount of the compound represented by the formula (III).

[7.4] The production method according to any one of the above items [4], [5], [6], [7], [7.1], [7.2] and [7.3], wherein the phosphate is used in an amount of 1.0 to 5.0-fold mol (more preferably 1.8 to 2.2-foldmol) based on the amount of the compound represented by the formula (III).

[7.5] The production method according to any one of the above items [4], [5], [6], [7], [7.1], [7.2], [7.3] and [7.4], wherein the amine compound is used in an amount of 0.001 to 1.0-fold mol (more preferably 0.38 to 0.42-fold mol) based on the amount of the compound represented by the formula (III).

[8] A compound represented by following formula, or a salt thereof, or a solvate thereof:

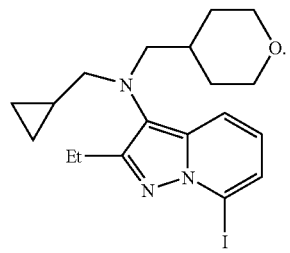

[9] A compound (II) represented by following formula

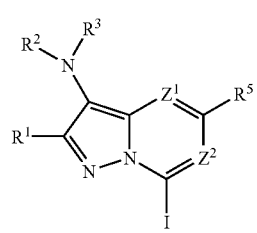

(wherein $Z^1$, $Z^2$, $R^1$, $R^2$, $R^3$ and $R^5$ have the same definitions as described in the above item [1] for $Z^1$, $Z^2$, $R^1$, $R^2$, $R^3$ and $R^5$ respectively), a salt thereof, or a solvate thereof.

Effect Of Invention

1. Crystalline substrates, pyrazole-fused ring derivatives (such as 7-iodopyrazolo[1,5-a]pyridine derivatives and the like) which can be isolated and purified without using column chromatography, or salts thereof or solvates thereof have been found.

2. An iodination reaction of a pyrazole-fused ring derivative (such as pyrazolo[1,5-a]pyridine derivative and the like) using pentafluoroiodobenzene which can be handled easily in industrial production and showing excellent yield has been found.

3. A method has been found which can recover again pentafluoroiodobenzene used as a reagent, by a treatment using iodine after the reaction.

4. A method of introducing a nitrogen substitutent into a pyrazole-fused ring derivative (such as pyrazolo[1,5-a]pyridine derivative and the like) using an amidation coupling reaction has been newly found.

That is, there has been provided (1) a method for producing a pyrazole-fused ring derivative (such as pyrazolo[1,5-a]pyridine derivative and the like), and (2) pyrazole-fused ring derivatives (such as 7-iodopyrazolo[1,5-a]pyridine derivatives and the like) or salts thereof or solvates thereof, which are useful as a synthesis intermediate of a pyrazole-fused ring derivative (the above-described 7-phenylpyrazolo[1,5-a]pyridine derivative and the like) having a CRF receptor antagonistic action.

PREFERRED EMBODIMENTS TO CARRY OUT THE PRESENT INVENTION

The present invention will be described in detail hereinafter.

Several of the structural formulas given for compounds throughout the present specification will represent a specific isomer for convenience, but the invention is not limited to such specific isomers and encompasses all isomers and isomer mixtures, including geometric isomers, asymmetric carbon-derived optical isomers, stereoisomers and tautomers, implied by the structures of the compounds.

Further, the compounds of the present invention may form salts, and the compounds of the present invention may encompass anhydrates, hydrates, or solvates of the salts. Unless stated otherwise, the compounds of the present invention may be, but are not limited to, crystalline or noncrystalline.

Throughout the present specification, "n-" signifies "normal", "sec-" signifies "secondary", and "tert-" and "t-" both signify "tertiary".

[Definition of $Z^1$ and $Z^2$]

$Z^1$ and $Z^2$ each independently represents a methine group or a nitrogen atom. Preferably, $Z^1$ and $Z^2$ represent a methine group, or one of $Z^1$ and $Z^2$ represents a methine group and another represents a nitrogen atom. More preferably, $Z^1$ and $Z^2$ represent a methine group, or $Z^1$ represents a nitrogen atom and $Z^2$ represents a methine group. Further preferably, $Z^1$ and $Z^2$ represent a methine group.

[Definition of $R^5$]

$R^5$ represents a hydrogen atom or a $C_{1-6}$ alkyl group, preferably a hydrogen atom.

[Definition of $R^1$]

$R^1$ represents a group represented by the formula —$R^{10}$—$R^{11}$ (wherein $R^{10}$ represents a single bond, an oxygen or sulfur atom; and $R^{11}$ represents a methyl or ethyl group) or a methoxymethyl group. Preferred example thereof may include a methyl, ethyl, methoxy, methylthio, ethoxy or methoxymethyl group, and more preferably an ethyl, methoxy or methylthio group, and most preferably an ethyl group.

[Definitions of $R^2$ and $R^3$]

$R^2$ and $R^3$ each independently represents a hydrogen atom, a t-butoxycarbonyl group, or a group represented by the formula —$X^{21}$—$X^{31}$ (wherein $X^{21}$ represents a methylene or carbonyl group; and $X^{31}$ represents a $C_{1-6}$alkyl, $C_{3-8}$ cycloalkyl, tetrahydropyran-yl or tetrahydrofuran-yl group).

Preferably, $R^2$ and $R^3$ each independently represents a n-propyl, n-butyl, (cyclobutyl)methyl, cyclopropylmethyl, (tetrahydropyranyl)methyl or (tetrahydrofuranyl)methyl group. More preferably, $R^2$ and $R^3$ each independently represents a cyclopropylmethyl, (4-tetrahydropyranyl)methyl, (3-tetrahydrofuranyl)methyl or (2-tetrahydrofuranyl)methyl group. Even more preferably, $R^2$ may represent a cyclopropylmethyl or (4-tetrahydropyranyl)methyl group, and most preferably $R^2$ may represent a cyclopropylmethyl group and $R^3$ may represent a (4-tetrahydropyranyl)methyl group.

[Definition of X]

X represents a releasing group. X is not particularly limited, as long as it is a releasing group used in organic chemical reactions. X may represent, preferably, a bromine atom, an iodine atom or a $C_{1-6}$ alkylsulfonyloxy group optionally substituted with 1 to 5 halogen atoms, more preferably, a bromine atom, an iodine atom or a trifluoromethylsulfonyloxy group, further preferably an iodine atom.

[Definitions of $R^{20}$ and $R^{30}$]

$R^{20}$ and $R^{30}$ each independently represents a hydrogen atom, or a group represented by the formula —$X^{22}$—$X^{32}$ (wherein $X^{22}$ represents a methylene or carbonyl group; and $X^{32}$ represents a $C_{1-6}$ alkyl, $C_{3-8}$ cycloalkyl, tetrahydropyran-yl or tetrahydrofuran-yl group).

Preferably, $R^{20}$ represents a hydrogen atom and $R^{30}$ represents a group represented by the formula —$X^{42}$—$X^{32}$ (wherein $X^{42}$ represents a carbonyl group; and $X^{32}$ represents a $C_{1-6}$ alkyl, $C_{3-8}$ cycloalkyl, tetrahydropyran-yl or tetrahydrofuran-yl group). More preferably, $R^{20}$ represents a hydrogen atom and $R^{30}$ represents a 4-tetrahydropyranylcarbonyl group.

[Definition of $R^4$]

$R^4$ represents a hydrogen atom, a chlorine atom, a bromine atom, an iodine atom or a group represented by the following formula:

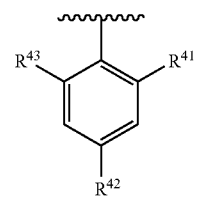

wherein $R^{41}$, $R^{42}$ and $R^{43}$ each independently represents (1) a hydrogen atom; (2) a halogen atom; (3) a $C_{1-6}$ alkoxy group which may have one or two selected from the group consisting of a fluorine atom, a chlorine atom, a bromine atom, a cyano group, a $C_{1-6}$ alkoxy group, a pyrrolidinyl group, a piperazinyl group, a piperidyl group, a morpholinyl group, a $C_{3-8}$ cycloalkyl group, a tetrahydropyran-yl group or a tetrahydrofuran-yl group; or (4) a $C_{1-6}$ alkyl group which may have one or two selected from the group consisting of a fluorine atom, a chlorine atom, a bromine atom, a cyano group, a $C_{1-6}$ alkoxy group, a pyrrolidinyl group, a piperazinyl group, a piperidyl group, a morpholinyl group, a $C_{3-8}$ cycloalkyl group, a tetrahydropyran-yl group and a tetrahydrofuran-yl group. As preferred examples of $R^{41}$, $R^{42}$ and $R^{43}$, two of $R^{40}$, $R^{41}$ and $R^{42}$ may represent methoxy groups, and more preferably, $R^{40}$ and $R^{42}$ may represent methoxy groups.

More preferably, $R^4$ represents a hydrogen atom.

The term "pyrrolidinyl group" used herein refers to a monovalent substitutent by removing a hydrogen atom from pyrrolidine, specifically, for example, a 1-pyrrolidinyl, 2-pyrrolidinyl or 3-pyrrolidinyl group.

The term "piperazinyl group" used herein refers to a monovalent substitutent by removing a hydrogen atom from piperazine, specifically, for example, a 1-piperazinyl, 2-piperazinyl, 3-piperazinyl or 4-piperazinyl group.

The term "piperidyl group" used herein refers to a monovalent substitutent by removing a hydrogen atom from piperidine, specifically, for example, a 1-piperidyl, 2-piperidyl, 3-piperidyl or 4-piperidyl group.

The term "morpholinyl group" used herein refers to a monovalent substitutent by removing a hydrogen atom from morpholine, specifically, for example, a 2-morpholinyl, 3-morpholinyl or 4-morpholinyl group.

The term "tetrahydropyran-yl group" used herein refers to a monovalent substitutent by removing a hydrogen atom from tetrahydropyran, specifically, for example, a tetrahydropyran-2-yl, tetrahydropyran-3-yl or tetrahydropyran-4-yl group. Preferably it may be a tetrahydropyran-4-yl group represented by following formula:

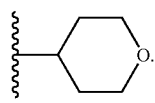

The term "tetrahydrofuran-yl group" used herein refers to a monovalent substitutent by removing a hydrogen atom from tetrahydrofuran, specifically, for example, a tetrahydrofuran-2-yl or tetrahydrofuran-3-yl group. Preferably it may be a tetrahydrofuran-3-yl group represented by following formula:

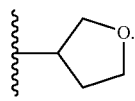

A (4-tetrahydropyranyl)methyl group used herein refers to a methyl group substituted with an aforementioned tetrahydropyran-4-yl group.

A (2-tetrahydrofuranyl)methyl group used herein refers to a methyl group substituted with an aforementioned tetrahydrofuran-2-yl group.

A (3-tetrahydrofuranyl)methyl group used herein refers to a methyl group substituted with an aforementioned tetrahydrofuran-3-yl group.

"$C_{1-6}$alkyl group" used herein refers to a linear or branched alkyl group having 1 to 6 carbon atoms. Examples thereof may include a methyl, ethyl, 1-propyl (n-propyl), 2-propyl (iso-propyl), 2-methyl-1-propyl (iso-butyl), 2-methyl-2-propyl (tert-butyl), 1-butyl (n-butyl), 2-butyl (sec-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, 2,3-dimethyl-2-butyl group or the like.

"$C_{3-10}$cycloalkyl group" used herein refers to a monocyclic or bicyclic aliphatic hydrocarbon group having 3 to 10 carbon atoms. Examples thereof may include a cyclopropyl, cyclobutyl, cyclopentyl, cyclohexyl, cycloheptyl, cyclooctyl, cyclononyl and cyclodecyl group, preferably a cyclopropyl, cyclobutyl and cyclopentyl group, and more preferably a cyclopropyl group.

"$C_{1-6}$ alkoxy group" used herein refers to a group having an oxygen atom bonded to the end of the aforementioned "$C_{1-6}$ alkyl group". Examples thereof may include a methoxy, ethoxy, 1-propoxy (n-propoxy), 2-propoxy (iso-propoxy), 2-methyl-1-propoxy (iso-butoxy), 2-methyl-2-propoxy (t-butoxy), 1-butoxy (n-butoxy), 2-butoxy(sec-butoxy), 1-pentyloxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, 2,3-dimethyl-2-butoxy group or the like.

The solvation in the compound (II) according to the present invention or salts thereof or solvates thereof is not particularly limited, as long as a solvation is formed with the compound (II) of the present invention or salts thereof. A solvent forms a solvation at an appropriate ratio of 0.1 to 5 molecules based on one molecule of the compound. The solvent in the solvation includes 1 to 3 solvents selected from the group consisted of dimethyl carbonate, diethyl carbonate, methyl acetate, ethyl acetate, isopropyl acetate, isopropanol, n-propanol and ethanol (in the case of combination of a plurality of compounds, mixtures of any ratio), and the like, and preferably solvation with dimethyl carbonate and isopropanol (mixture of any ratio), and the like.

The salts of compound (II) according to the present invention may not be particularly restricted so long as they are salts formed with the compound (II) of the invention. Examples thereof may be salts with inorganic acids, salts with organic acids and salts with acidic amino acids, among which pharmacologically acceptable salts are preferable. The acids may form salts at appropriate ratios of 0.1-5 molecules based on one molecule of the compound.

Preferred examples of salts with inorganic acids may include salts of hydrochloric acid, hydrobromic acid, sulfuric acid, nitric acid, phosphoric acid and the like. As preferred examples of salts with organic acids, there may be salts of acetic acid, succinic acid, fumaric acid, maleic acid, tartaric acid, citric acid, lactic acid, stearic acid, benzoic acid, methanesulfonic acid, p-toluenesulfonic acid and the like.

Preferred examples of salts with acidic amino acids may include salts with aspartic acid, glutamic acid and the like.

Preferred examples of salts of compound (II) according to the present invention may include salts with hydrochloric acid, sulfuric acid, methanesulfonic acid, p-toluenesulfonic acid, or hydrobromic acid, more preferably salts with hydrochloric acid or p-toluenesulfonic acid.

The production method according to the present invention will be illustrated in detail.

In the following formulae, $Z^1$, $Z^2$, $R^1$, $R^2$, $R^3$, $R^4$, $R^5$, $R^{20}$, $R^{30}$ and $X^1$ have the same definitions as those for the $Z^1$, $Z^2$, $R^1$, $R^2$, $R^3$, $R^4$, $R^5$, $R^{20}$, $R^{30}$ and X.

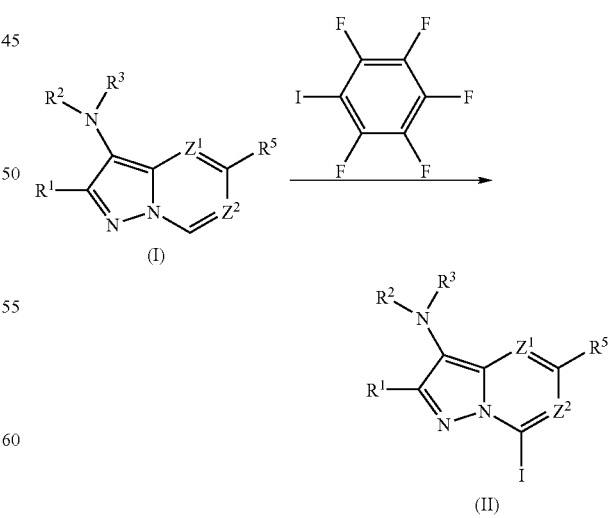

The step 1A is a step in which a compound (I) is anionated using an organometallic reagent, and the resulting product is reacted with pentafluoroiodobenzene to obtain a compound (II). Conditions for the reaction, treatment, purification and the like in the step 1A will be described below, and specifically, the reaction can be carried out referring to the following Production Examples 6, 14 and 15 as a specific example.

The compound (I) can be produced by methods described in the following Examples 3, 4 and 5, WO02/088121, WO03/078435, WO 00/59908, WO 00/59907 and the like.

The anionation reaction of a compound (I) using an organometallic reagent and the reaction of the anionated compound (I) with pentafluoroiodobenzene are carried out in an organic solvent such as ether solvents such as tetrahydrofuran, 1,2-dimethoxyethane, methyl t-butyl ether, cyclopentyl methyl ether, diethyl ether, diisopropyl ether, dibutyl ether, dicyclopentyl ether and the like; hydrocarbon-based aromatic ring solvents such as benzene, toluene and the like; hydrocarbon-based solvents such as heptane, hexane and the like. Suitable examples of the organic solvent may include ether solvents and the like, and more suitable examples thereof may include tetrahydrofuran and the like.

The anionation reaction of a compound (I) using an organometallic reagent and the reaction of the anionated compound (I) with pentafluoroiodobenzene are carried out at 0° C. (inner temperature in a reaction vessel) or lower, and preferably, the reaction can be carried out at −30° C. (inner temperature in a reaction vessel) or lower using a dry ice-ethanol bath and the like, and more preferably, the reaction can be carried out at −30 to −75° C., further preferably, the reaction can be carried out at −40 to −75° C.

The anionation reaction of a compound (I) using an organometallic reagent can be carried out by dropping an organometallic reagent into a solution of a compound (I) in the organic solvent, or dropping a solution prepared by dissolving a compound (I) in the organic solvent, into a solution of an organometallic reagent in the organic solvent.

The organometallic reagent means an organolithium compound (n-butyllithium, t-butyllithium, sec-butyllithium, phenyllithium, lithiumdiisopropylamide and the like), organomagnesium compound (butylmagnesium bromide, isopropyl magnesium bromide and the like), organic alkaline earth metal compound or the like. Suitable examples of the organometallic reagent may include organolithium compounds.

More suitable examples thereof may include n-butyllithium, t-butyllithium and sec-butyllithium, and further suitable examples thereof may include n-butyllithium.

The organometallic reagent can be used in an amount of 1.0 to 2.0-fold mol, preferably 1.4 to 1.6-fold mol, more preferably 1.5-fold mol, based on a compound (I).

Although the reaction time of the anionation reaction of a compound (I) using the organometallic reagent is not particularly limited, it is preferable to effect stirring for 30 minutes to 2 hours at the reaction temperature after adding the reagent, and more preferably, stirring is effected for about 1 hour.

The reaction of the anionated compound (I) with pentafluoroiodobenzene can be carried out by dropping a solution of pentafluoroiodobenzene in the organic solvent, into a solution of the anionated compound (I) in the organic solvent, or dropping a solution of the anionated compound (I) in the organic solvent, into a solution of pentafluoroiodobenzene in the organic solvent. Suitably, the reaction is carried out by dropping a solution of pentafluoroiodobenzene in the organic solvent, into a solution of the anionated compound (I) in the organic solvent.

Pentafluoroiodobenzene can be used in an amount of 1.0 to 2.0-foldmol, preferably 1.4 to 1.6-foldmol, more preferably 1.5-fold mol, based on a compound (I).

Although the reaction time of the anionated compound (I) with pentafluoroiodobenzene is not particularly limited, it is preferable to effect stirring for 30 minutes to 2 hours at the reaction temperature after adding the reagent, and more preferably, stirring is effected for about 1 hour.

After the reaction of the anionated compound (I) with pentafluoroiodobenzene, (1) water, (2) water and tetrahydrofuran, or in some cases, (3) iodine and the like, are added at the reaction temperature, or at temperatures from the reaction temperature to room temperature.

In a case where iodine is added, thereafter, (2) water and tetrahydrofuran, sodium thiosulfate aqueous solution and the like are added. Iodine can be used in an amount of 1.0 to 2.0-fold mol, preferably 1.4 to 1.6-fold mol, more preferably 1.5-fold mol, based on pentafluoroiodobenzene.

After the reaction treatment, if desired, (1) usual extraction treatment with an organic solvent/water, drying of the organic solvent over anhydrous magnesium sulfate and the like, and distillation off of a solution of the solvent, (2) purification by column chromatography and purification by re-crystallization from an appropriate solvent, (3) filtration of a product generated by adding an organic solvent and water (mixture of acetonitrile and water), and the like can be appropriately combined, to obtain an intended compound.

As the organic solvent in the extraction treatment with an organic solvent/water, heptane, toluene, methyl t-butyl ether, ethyl acetate, methyl acetate, and halogen solvents such as dichloromethane, chloroform and the like can be used. This extraction treatment can be conducted after rendering an aqueous layer acidic with an acidic aqueous solution such as 5N-hydrochloric acid and the like, or can be conducted after rendering an aqueous layer alkaline with an alkaline aqueous solution such as a 5N sodium hydroxide aqueous solution and the like. Further, these treatments can be combined and the extraction treatment can be performed several times.

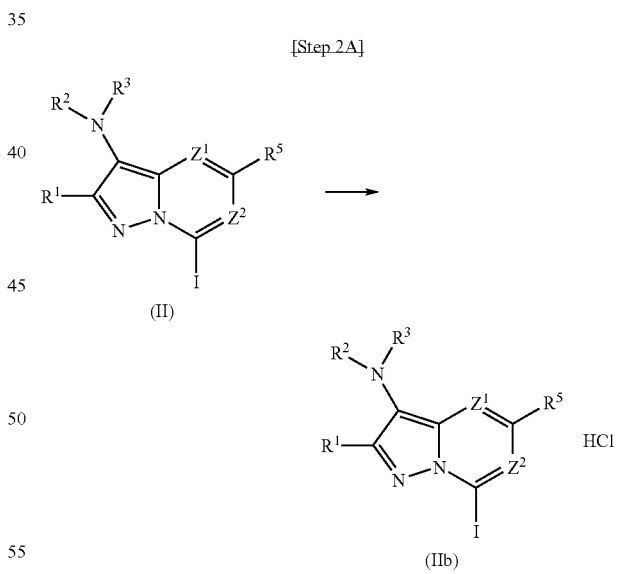

The step 2A is a step (hydrochloridation) for obtaining a compound (IIb) which is a hydrochloric acid body of a compound (II), from the compound (II).

Conditions for the reaction, treatment, purification and the like in the step 2A will be described below. Specifically, the reaction can be carried out referring to the following Production Example 7 as a specific example.

The compound (II) can be produced by methods described in WO 02/088121, WO 03/078435, WO 00/59908, WO 00/59907 and the like.

A compound (II) is dissolved in an organic solvent (preferably dimethyl carbonate, diethyl carbonate and isopropanol, n-propanol and the like), then, a solution of hydrogen chloride is added and the resulting mixture is stirred at −10 to 90° C. (suitably at room temperature) for 1 to 24 hours (suitably 14 to 16 hours). Then, the mixture is set at temperatures of 20 to −10° C. (suitably 5 to −10° C.) In this procedure, the organic solvent may be additionally added appropriately.

Then, the mixture is further stirred for 1 to 10 hours (suitably 1 to 3 hours), and a precipitate in the mixture is filtrated off. The filtrated precipitate can be appropriately washed with dimethyl carbonate, diethyl carbonate, heptane, hexane or water and the like, to obtain an intended compound (IIb).

The compound (IIb) can be dried (under conditions of 50° C., reduced pressure and the like), if necessary.

The organic solvent to be used in the step of hydrochloridation may be dimethyl carbonate, diethyl carbonate, ethyl acetate, isopropanol, n-propanol, t-butyl methyl ether, heptane, hexane and the like, and combination thereof.

The solution of hydrogen chloride may be concentrated hydrochloric acid, diluted hydrochloric acid, hydrochloric acid ethyl acetate solution, hydrochloric acid methanol solution and the like.

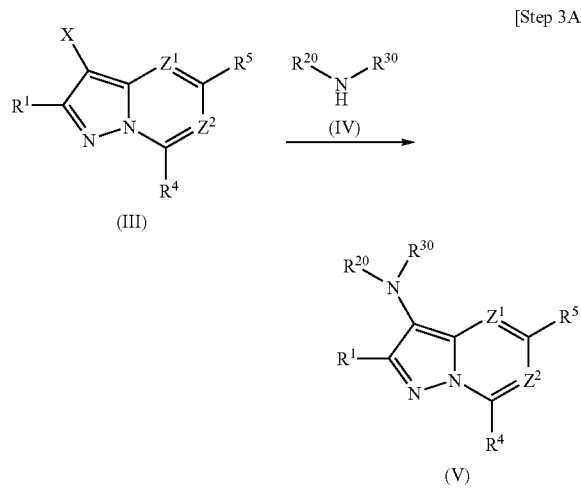

[Step 3A]

The step 3A is a step (amine coupling reaction) of reacting a compound (III) with a compound (IV) to obtain a compound (V) in the presence a metal catalyst, phosphate (alternatively, carbonate can be used instead of phosphate) and amine compound. Conditions for the reaction, treatment, purification and the like in the step 3A will be described below. Specifically, the reaction can be carried out referring to the following Production Example 3 as a specific example.

The compound (III) can be produced by methods described in the following examples, WO 02/088121, WO 03/078435 and the like.

As the compound (IV), there can be used compounds which is commercially available, and additionally, compounds produced from known carboxylic acid compounds, ester compounds, acid chloride compounds and the like using reaction conditions described in the following Production Example 2.

A metal catalyst, a phosphate, an amine compound, the compound (III) and the compound (IV) are dissolved in an organic solvent (toluene, xylene, diglyme, diethoxyethane, N,N-dimethylformamide, N-methylpyrrolidone and the like), and stirred at 50 to 200° C. (suitably 90 to 150° C., more suitably 110° C.) for 3 to 48 hours (suitably 14 to 16 hours).

The metal catalyst may be catalysts used in coupling reactions such as a copper catalyst or a palladium catalyst and the like. The metal catalyst may preferably be a copper catalyst.

The copper catalyst means copper (I) iodide, copper (II) iodide, copper (I) bromide, copper (II) bromide, copper (I) chloride, copper (II) chloride, copper (I) acetate, copper (II) acetate, copper oxide or the like. A preferable example of the copper catalyst may be copper iodide.

The palladium catalyst is not particularly limited, as long as it is a catalyst used in a coupling reaction such as $Pd(OAc)_2$, $Pd_2(dba)_3$ and the like.

The phosphate means tripotassium phosphate, dipotassium hydrogen phosphate, trisodium phosphate, disodium hydrogen phosphate, trilithium phosphate, dilithium hydrogen phosphate or magnesium phosphate, or a hydrate thereof. Preferable examples of the phosphate may include tripotassium phosphate or hydrates thereof. More preferable examples thereof may include tripotassium phosphate hydrates. The carbonate may include sodium carbonate, potassium cabonate, or cesium carbonate, or hydrates thereof and the like.

The amine compound is not particularly limited, as long as it is an amine compound which can be used as a ligand in a coupling reaction performed using a copper catalyst or palladium catalyst. Preferably, the amine compound means 1,2-cyclohexanediamine, N,N'-dimethylethylenediamine, tetramethylethylenediamine, phenanthroline or the like. More preferable examples thereof may include 1,2-cyclohexanediamine and N,N'-dimethylethylenediamine, most preferably 1,2-cyclohexanediamine.

The compound (IV) can be used in an amount of 1.0 to 3.0-fold mol, preferably 1.0 to 1.5-fold mol, more preferably 1.5-fold mol, based on a compound (III).

The copper catalyst can be used in an amount of 0.001 to 1.0-fold mol, preferably 0.15 to 0.25-fold mol, more preferably 0.2-fold mol, based on a compound (III).

The phosphate can be used in an amount of 1.0 to 5.0-fold mol, preferably 1.5 to 2.5-fold mol, more preferably 2.0-fold mol, based on a compound (III). When a carbonate is used instead of the phosphate, the amount of the carbonate used may be the same as that for the phosphate.

The amine compound can be used in an amount of 0.001 to 1.0-fold mol, preferably 0.35 to 0.45-fold mol, more preferably 0.4-fold mol, based on a compound (III).

After reaction, water or warm water of 40 to 70° C. is added at the reaction temperature to room temperature (preferably 90 to 20° C.). Then, the reaction mixture is stirred for 1 hour to over night and day. Further, thereafter, ammonia water, ethylenediamine aqueous solution or the like is added into the reaction mixture, and the mixture was stirred for 30 minutes to 1 hour.

After the reaction treatment, if necessary, (1) usual extraction treatment with an organic solvent/water, drying of the organic solvent over magnesium sulfate and the like, and distillation off of a solution of the solvent, (2) purification by column chromatography and purification by re-crystallization from a suitable solvent, (3) filtration of a product generated by adding an organic solvent and water (mixture of acetonitrile and water), and the like, and the appropriate combination thereof can be conducted, to obtain an intended compound.

Ethyl acetate, t-butyl methyl ether, toluene and the like can be used for the organic solvent in the extraction treatment with an organic solvent/water. The extraction treatment can be carried out single time or several times. A method in which water is added to a reaction mixture, and filtration is performed can also be adopted for the reaction treatment.

EXAMPLES

The present invention will be illustrated in detail by way of the following examples, but is not limited to the examples.

Production Example 1

2-Ethyl-3-iodopyrazolo[1,5-a]pyridine

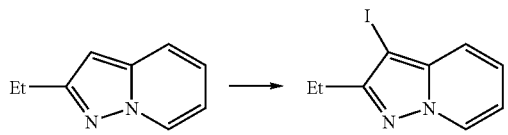

To a mixture of 2-ethylpyrazolo[1,5-a]pyridine (360 g, 2.46 mol), ethyl acetate (3600 mL), water (1800 mL) and sodium iodide (480 g, 3.20 mol, 1.3 equivalent) was added N-chlorosuccinimide (411 g, 3.08 mol) over a period of 30 minutes under cooling in an ice water bath, then, the reaction mixture was stirred at room temperature for 2 hours and 20 minutes. To the reaction mixture was added water and ethyl acetate, and the resulting mixture was extracted with ethyl acetate. The separated organic layer was washed twice with a 10% sodium thiosulfate aqueous solution, and concentrated under reduced pressure. To the resulting residue was added hexane, the residue was dissolved with heating. The hexane solution was filtrated to remove an insoluble substance. The hexane solution was washed with water, and concentrated under reduced pressure. Then, the resulting residue was dissolved in ethyl acetate, and the solvent was distilled off under reduced pressure, to obtain 663 g of a title compound (yield: 98.9%).

$^1$H NMR (400 MHz, CDCl$_3$) δ 1.35 (t, J=7.7 Hz, 3H), 2.84 (q, J=7.7 Hz, 2H), 6.72 (ddd, J=6.8, 6.8, 1.3 Hz, 1H), 7.15 (ddd, J=9.0, 6.8, 1.1 Hz, 1H), 7.37 (ddd, J=9.0, 1.3 Hz, 1.3, 1H) 8.36 (ddd, J=6.8, 1.1, 1.1 Hz, 1H).

Production Example 2

Tetrahydro-2H-pyran-4-carboxamide

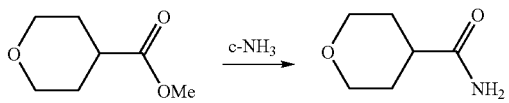

To methyl tetrahydro-2H-pyran-4-carboxylate (50 g, 347 mmol) was added concentrated ammonia water (50 mL), and the reaction mixture was stirred at room temperature for 43.5 hours. Thereafter, the reaction mixture was cooled in an ice water bath, and the precipitate was filtrated. Then, the precipitate was dried at 40° C. under reduced pressure, to obtain 33.4 g of a title compound (yield: 74.6%).

$^1$H NMR (400 MHz, DMSO-d$_6$) δ 1.45-1.62 (m, 4H), 2.28 (tt, J=11.1, 4.4 Hz, 1H) 3.26 (ddd, J=11.4, 11.4, 2.7 Hz, 2H), 3.82 (br d, J=11.4 Hz, 2H), 6.74 (br s, 1H), 7.21 (br s, 1H)

Production Example 3

N-(2-Ethyl-[1,5-a]pyridine-3-yl)tetrahydro-2H-pyran-4-carboxamide

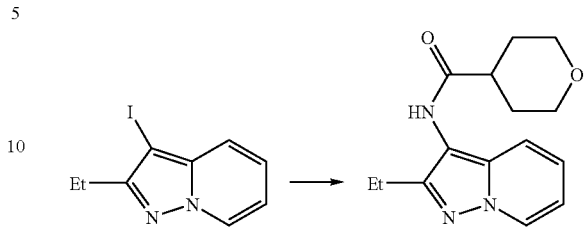

A mixture of 2-ethyl-3-iodopyrazolo[1,5-a]pyridine (350 g, 1.29 mol), tetrahydro-2H-pyran-4-carboxamide (249 g, 1.93 mmol), copper iodide (49.0 g, 258 mmol), tripotassium phosphate (hydrate) (546 g, 2.57 mol), 1,2-cyclohexanediamine (mixture of cis and trans) (58.7 g, 514 mmol) and xylene (3500 mL) was stirred for 6 hours at an outer temperature of 120° C. (oil bath). Heating was stopped, and when the inner temperature of the reaction mixture reached 61.5° C., hot water (3500 mL) of 58° C. was added to the reaction mixture, and the mixture was stirred overnight under the same condition. To the reaction mixture was added 28% ammonia water (1050 mL) and the mixture was stirred for 1 hour, and a precipitate was filtrated. The precipitate was washed with water (1750 mL) and ethyl acetate (1050 mL), and air-dried at 60° C. overnight, to obtain 280 g of a title compound (6:1 mixture of main conformer:sub conformer) (yield: 79.6%).

Main Conformer:
$^1$H NMR (400 MHz, CDCl$_3$) δ 1.33 (t, J=7.7 Hz, 3H), 1.88-2.05 (m, 4H), 2.57-2.67 (m, 1H), 2.75 (q, J=7.7 Hz, 2H), 3.50 (ddd, J=11.4, 11.4, 2.9 Hz, 2H), 4.09 (ddd, J=11.4, 4.0, 2.6 Hz, 2H), 6.68 (ddd, J=6.8, 6.8, 1.3 Hz, 1H), 6.82 (br s, 1H), 7.07 (ddd, J=9.0, 6.8, 1.3 Hz, 1H), 7.29 (br d, J=9.0 Hz, 1H) 8.30 (d, J=6.8 Hz, 1H).

Sub Conformer:
$^1$H NMR (400 MHz, CDCl$_3$) δ 1.34 (t, J=7.7 Hz, 3H), 1.40-1.50 (m, 2H), 1.88-2.05 (m, 2H), 2.37-2.48 (m, 1H), 2.78 (q, J=7.7 Hz, 2H), 3.14 (ddd, J=11.9, 11.9, 1.8 Hz, 2H), 3.84-3.92 (m, 2H), 6.56 (br s, 1H), 6.80 (ddd, J=6.8, 6.8, 1.3 Hz, 1H), 7.20 (br dd, J=9.0, 6.8 Hz, 1H), 7.34 (br d, J=9.0 Hz, 1H), 8.39 (d, J=6.8 Hz, 1H).

Production Example 4

N-Cyclopropylmethyl-N-(2-ethyl-[1,5-a]pyridine-3-yl)-tetrahydro-2H-pyran-4-carboxamide

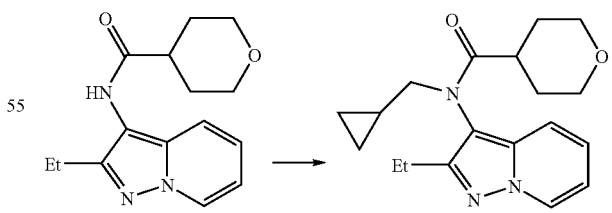

A mixture of N-(2-ethyl-[1,5-a]pyridine-3-yl)tetrahydro-2H-pyran-4-carboxamide (272 g, 915 mmol), potassium t-butoxide (144 g, 1.28 mmol) and 1,2-dimethoxyethane (1750 mL) was stirred at an outer temperature of 40° C. Into the reaction mixture, (bromomethyl)cyclopropane (161 g, 1.19 mol) was dropped so that the inner temperature was 50° C. or lower. The reaction mixture was stirred with heating for 4 hours, and into the reaction mixture was added water (1250 mL) and toluene (3750 mL). An aqueous layer of the reaction mixture was removed, then, an organic layer was washed sequentially with 10% saline (1250 mL) and water (1250 mL×2), and the solvent was concentrated under reduced pressure, to obtain 277 g of a title compound as brown oil (yield: 92.6%).

$^1$H NMR (400 MHz, CDCl$_3$) δ 0.03-0.11 (m, 1H), 0.14-0.22 (m, 1H) 0.32-0.46 (m, 2H), 0.85-0.98 (m, 1H), 1.36 (t, J=7.6 Hz, 3H) 1.29-1.40 (m, 1H), 1.40-1.50 (m, 1H), 1.85 (ddd, J=16.3, 11.9, 4.4 Hz, 1H), 1.97 (ddd, J=16.5, 11.9, 4.6 Hz, 1H), 2.41 (tt, J=11.5, 3.8 Hz, 1H), 2.66-2.84 (m, 2H), 3.03 (ddd, J=11.9, 11.9, 2.2 Hz, 1H), 3.15 (ddd, J=11.9, 11.9, 2.2 Hz, 1H), 3.31 (dd, J=13.7, 7.3 Hz, 1H), 3.79 (dd, J=13.7, 7.3 Hz, 1H), 3.76-3.86 (m, 1H), 3.91 (ddd, J=11.9, 4.4, 2.0 Hz, 1H), 6.79 (ddd, J=6.8, 6.8, 1.4 Hz, 1H), 7.17 (br dd, J=8.8, 6.8 Hz, 1H), 7.33 (br d, J=8.8 Hz, 1H), 8.40 (d, J=6.8 Hz, 1H).

Production Example 5

N-Cyclopropylmethyl-N-(2-ethylpyrazolo[1,5-a]pyridine-3-yl)-N-(tetrahydro-2H-4-pyranylmethyl)amine

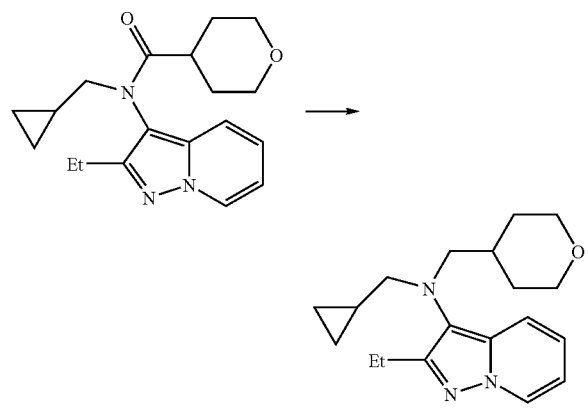

A solution of N-cyclopropylmethyl-N-(2-ethyl-[1,5-a]pyridine-3-yl)tetrahydro-2H-pyran-4-carboxamide (220 g, 672 mmol) in tetrahydrofuran (1100 mL) was stirred at an outer temperature of 55° C. (warm bath). Into the reaction mixture, a borane-tetrahydrofuran complex (BH$_3$-THF) (1M solution, 1748 mL) was dropped. The mixture was further stirred with heating for 2 hours, and the reaction mixture was cooled in an ice water bath. To the reaction mixture was added 2N hydrochloric acid (437 mL). Thereafter, the reaction mixture was further stirred for 1 hour at an outer temperature of 50° C. (hot water bath). After the reaction, into the reaction mixture was dropped a 5N sodium hydroxide aqueous solution (299 mL) to give pH 8, and an aqueous layer was removed. To an organic layer was added toluene (2200 mL), then, the organic layer was washed twice with water, and the solvent was concentrated under reduced pressure, to obtain 209 g of a title compound (yield: 99.2%).

$^1$H NMR (400 MHz, CDCl$_3$) δ −0.04-0.06 (m, 2H), 0.30-0.40 (m, 2H) 0.73-0.86 (m, 1H), 1.18-1.36 (m, 2H), 1.33 (t, J=7.6 Hz, 3H) 1.46-1.60 (m, 1H), 1.72 (br d, J=12.8 Hz, 2H), 2.82 (q, J=7.6 Hz, 2H), 2.84 (d, J=7.2 Hz, 2H), 3.01 (d, J=7.2 Hz, 2H), 3.28 (ddd, J=12.0, 12.0, 2.0 Hz, 2H), 3.92 (br dd, J=12.0, 4.4 Hz, 2H), 6.59 (ddd, J=6.8, 6.8, 1.2 Hz, 1H), 6.95 (ddd, J=8.8, 6.8, 1.2 Hz, 1H), 7.44 (ddd, J=8.8, 1.2, 1.2 Hz, 1H) 8.29 (ddd, J=6.8, 1.2, 1.2 Hz, 1H).

Production Example 6

N-Cyclopropylmethyl-N-(2-ethyl-7-iodopyrazolo[1,5-a]-pyridine-3-yl)-N-(tetrahydro-2H-4-pyranylmethyl)amine

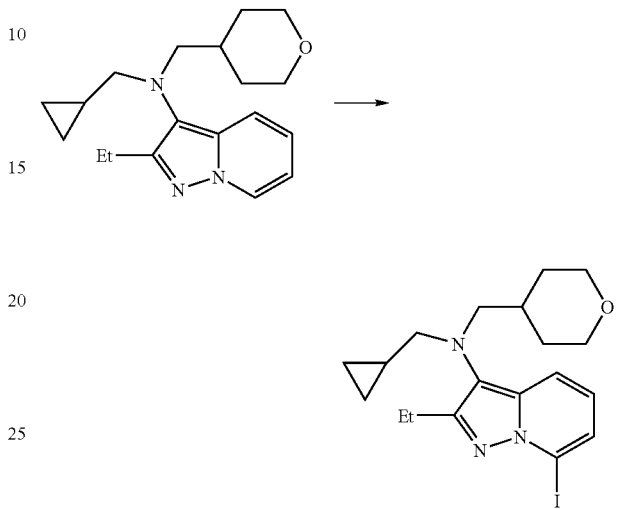

A solution of N-cyclopropylmethyl-N-(2-ethylpyrazolo[1,5-a]pyridine-3-yl)-N-(tetrahydro-2H-4-pyranylmethyl)amine (180 g, 574 mmol) in tetrahydrofuran (1620 mL) was cooled in a dry ice-ethanol bath. Into the reaction mixture was dropped n-butyllithium (1.6M hexane solution; 538 mL, 854 mmol) at an inner temperature of −73° C. to −64.5° C. At the same temperature, the reaction mixture was stirred for 1 hour, and into the reaction mixture was dropped pentafluoroiodobenzene (115 mL, 861 mmol). The reaction mixture was further stirred for 1 hour and 20 minutes at the same temperature, and to the reaction mixture was added water/tetrahydrofuran (1/1, v/v, 360 mL). Into the reaction mixture was added water (3600 mL) and heptane (3600 mL). An aqueous layer was removed, and an organic layer was washed with water (3600 mL). Then, to the organic layer was added 5N hydrochloric acid (1800 mL) and the aqueous layer was separated. Then, the aqueous layer was cooled in an ice water bath, and a 5N sodium hydroxide aqueous solution (1620 mL) was added, then, toluene (3600 mL) was added, and an organic layer was separated. The remaining aqueous layer was further extracted with toluene (3600 mL), and both the organic layers were combined. The solution was concentrated under reduced pressure, to obtain 220 g of a title compound as deep green oil (yield: 87.3%).

$^1$H NMR (400 MHz, CDCl$_3$) δ −0.02-0.05 (m, 2H), 0.33-0.40 (m, 2H), 0.74-0.86 (m, 1H), 1.19-1.32 (m, 2H), 1.36 (t, J=7.6 Hz, 3H), 1.46-1.60 (m, 1H), 1.71 (br d, J=13.2 Hz, 2H), 2.86 (d, J=6.8 Hz, 2H), 2.88 (q, J=7.6 Hz, 2H), 3.02 (d, J=6.8 Hz, 2H) 3.28 (ddd, J=11.6, 11.62.0 Hz, 2H), 3.92 (br dd, J=11.6, 2.6 Hz, 2H), 6.71 (dd, J=8.8, 6.8 Hz, 1H), 7.20 (dd, J=6.8, 1.2 Hz, 1H), 7.47 (dd, J=8.8, 1.2 Hz, 1H).

Production Example 7

N-Cyclopropylmethyl-N-(2-ethyl-7-iodopyrazolo[1,5-a]-pyridine-3-yl)-N-(tetrahydro-2H-4-pyranylmethyl)amine hydrochloride

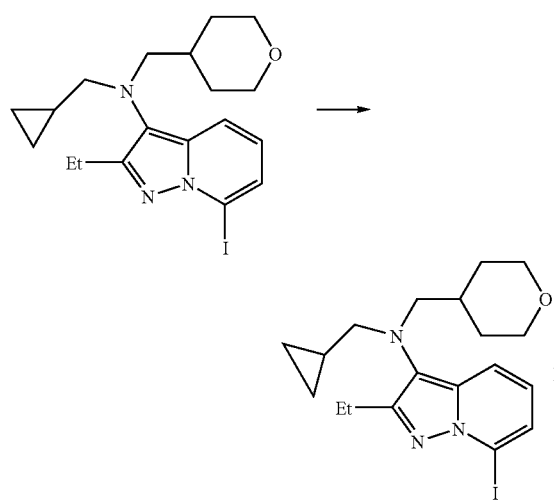

Into a solution of N-cyclopropylmethyl-N-(2-ethyl-7-iodopyrazolo[1,5-a]pyridin e-3-yl)-N-(tetrahydro-2H-4-pyranylmethyl)amine (220 g, 501 mmol) in dimethyl carbonate (3600 mL) was dropped a solution of concentrated hydrochloric acid (48.5 mL, 575 mmol) in isopropanol (270 mL) at room temperature over a period of 20 minutes, and the mixture was further stirred at room temperature for about 15 hours. The reaction mixture was cooled in an ice water bath, and to the reaction mixture was added dimethyl carbonate (900 mL). This mixture was stirred for about 5 hours, and a precipitate was filtrated. The precipitate was washed with dimethyl carbonate (900 mL), and dried at 50° C. under reduced pressure, to obtain 250 g of a title compound as a solvate in dimethyl carbonate and isopropanol (yield: 93.7%).

$^1$H NMR (400 MHz, CD$_3$OD) δ 0.08-0.40 (m, 2H), 0.42-0.56 (m, 2H), 0.81-0.94 (m, 1H), 1.30-1.60 (m, 4H), 1.50 (t, J=7.5 Hz, 3H), 1.67-1.81 (m, 1H), 3.06 (q, J=7.5 Hz, 2H), 3.24 (ddd, J=11.7, 11.72.4 Hz, 2H), 3.56-3.76 (m, 4H), 3.82-3.90 (m, 2H), 7.20 (dd, J=8.8, 7.1 Hz, 1H), 7.66 (d, J=7.1 Hz, 1H), 7.98 (d, J=8.8 Hz, 1H).

Production Example 8

2-Bromo-1,3-dimethoxy-5-(methoxymethyl)benzene

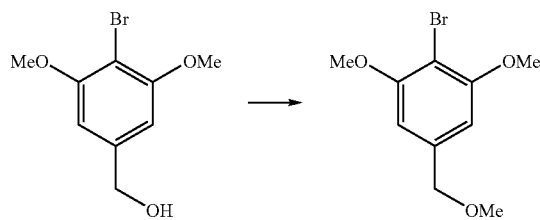

Under cooling in an ice water bath, to a solution of (4-bromo-3,5-dimethoxyphenyl)methanol (100 g, 405 mmol) and triethylamine (67.5 mL, 484 mmol) in dimethoxyethane (1000 mL) was added mesyl chloride (34.5 mL, 446 mmol), and the reaction mixture was further stirred for 30 minutes. Then, to the reaction mixture was added a 28% sodium methoxide methanol solution (350 mL, 1.72 mol), and the reaction mixture was stirred at room temperature for 3 hours. After the reaction, toluene (1000 mL) and water (1000 mL) were added to the reaction mixture, then, an aqueous layer was removed, and an organic layer was washed sequentially with water (1000 mL), 1N hydrochloric acid (500 mL) and water (500 mL), then, the solvent was concentrated under reduced pressure, to obtain 105 g of a title compound as colorless oil (yield: 99.5%).

Production Example 9

2,6-Dimethoxy-4-(methoxymethyl)phenylboric acid

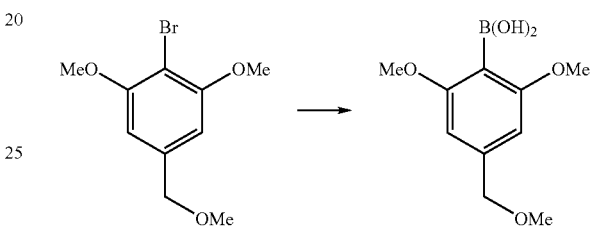

Under cooling in an dry ice-acetone bath in nitrogen flow, to a solution of 2-bromo-1,3-dimethoxy-5-(methoxymethyl)benzene (20.0 g, 76.6 mmol) in tetrahydrofuran (200 mL) was added a solution (50.9 mL, 80.4 mmol) of 1.58Mn-butyllithiumin hexane, and the reaction mixture was stirred for 30 minute. Then, to the reaction mixture was added a solution of trimethoxyborane (8.75 g, 84.2 mmol) in tetrahydrofuran (20 mL), and the reaction temperature was raised up to 0° C. under stirring. To the reaction mixture was added 1N hydrochloric acid (200 mL), and the reaction mixture was stirred for 30 minutes at room temperature. After the reaction, to the reaction mixture was added toluene (200 mL) and an organic layer was separated, then, the remaining aqueous layer was further extracted with toluene (100 mL). Combined organic layers were washed with water (100 mL), and the solvent was concentrated under reduced pressure. The resulting residue was dissolved in t-butyl methyl ether (75 mL), the reaction mixture was stirred for 30 minutes. Then, to this was added heptane (223 mL), and the mixture was further stirred for 2 hours. A precipitate was filtrated, and the precipitate was washed with a t-butyl methyl ether-heptane mixed solution (1:3, 3.75 mL), and dried at 40° C. for 24 hours to obtain 12.4 g of a title compound (yield: 71.8%).

Production Example 10

Methyl 4-bromo-3,5-dimethoxybenzoate

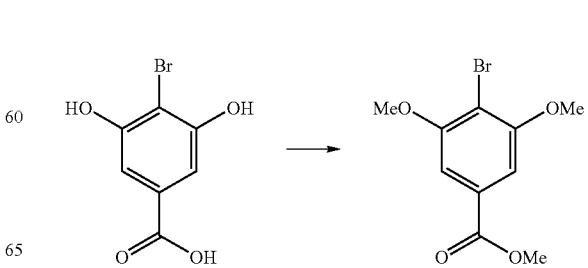

Under cooling in an ice water bath, to a solution of 4-bromo-3,5-dihydroxybenzoic acid (127.5 g) in N,N-dimethylformamide (1020 mL) were added potassium carbonate (359 g), and iodomethane (143 mL). Then, the reaction mixture was stirred at room temperature for 17 hours, and the reaction mixture was poured into ice water. Precipitated solid was filtrated, and the precipitate was washed with water. Then, the residue was dissolved in ethyl acetate, then, the solution was dried over anhydrous magnesium sulfate, and the solvent was distilled off under reduced pressure, to obtain 133.2 g of a title compound as white solid.

Production Example 11

(4-Bromo-3,5-dimethoxyphenyl)methanol

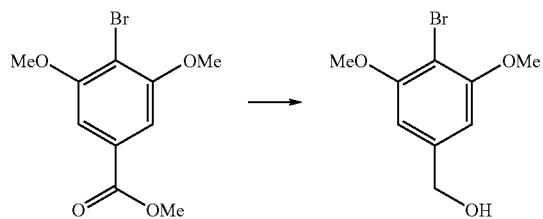

To a solution of methyl 4-bromo-3,5-dimethoxybenzoate (133.2 g) in tetrahydrofuran (500 mL) was added lithium borohydride (20.8 g) slowly at room temperature, and the mixture was further stirred for 3 hours under reflux with heating. The reaction mixture was cooled down to room temperature, and ice water (1.5 L) and ethyl acetate (1.2 L) were added, and extraction with ethyl acetate was performed. The resultant organic layer was washed with saturated saline, and dried over anhydrous magnesium sulfate, and the solvent was distilled off under reduced pressure, to obtain 118.8 g of a title compound as white solid.

Production Example 12

2-Bromo-1,3-dimethoxy-5-(methoxymethyl)benzene

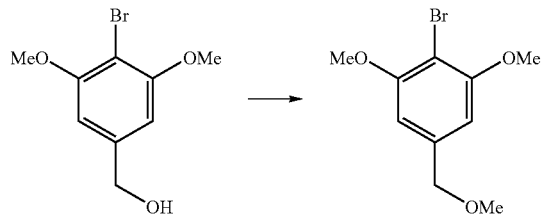

Under cooling in an ice water bath, to a solution of (4-bromo-3,5-dimethoxyphenyl)methanol (118.8 g) in N,N-dimethylformamide (960 mL) was added sodium hydride (60% oily; 24.7 g), and the mixture was stirred for 10 minutes. To this iodomethane (41.7 mL) was dropped. Thereafter, the reaction mixture was stirred at room temperature for 1 hour. The reaction mixture was poured into ice water (2.5 L), and extracted with ethyl acetate. The resulting organic layer was washed with saturated saline, and dried over anhydrous magnesium sulfate. The solvent was distilled off under reduced pressure. The resulting residue was purified by silica gel column chromatography, and from a fraction of n-hexane: ethyl acetate (4:1), 121.3 g of a title compound was obtained as colorless oil.

Production Example 13

2,6-Dimethoxy-4-(methoxymethyl)phenylboric acid

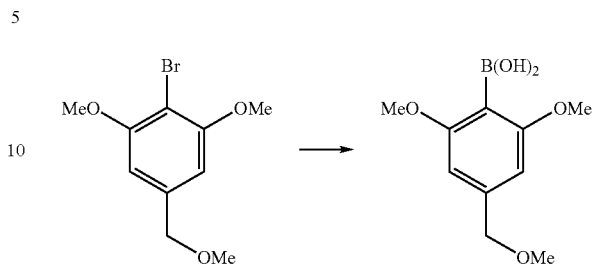

Into a Solution of 2-bromo-1,3-dimethoxy-5-(methoxymethyl)benzene (121.3 g) in tetrahydrofuran (730 mL), n-butyllithium (2.64M hexane solution; 182 mL) was dropped at −78° C., and the mixture was stirred for 20 minutes. To the reaction mixture was added a solution of trimethoxyborane (61.7 mL) in tetrahydrofuran (20 mL) at −78° C. The temperature was raised until the inner temperature of the reaction mixture reached −10° C., a saturated ammonium chloride aqueous solution (730 mL) was added, and the mixture was further stirred for 15 minutes. To the resulting reaction mixture was added ethyl acetate, extraction with ethyl acetate was performed, and the resulting organic layer was washed with saturated saline, and dried over anhydrous magnesium sulfate. The solvent was distilled off under reduced pressure. The resulting residue was purified by silica gel column chromatography, and from a fraction of n-hexane:ethyl acetate (2:3), 90.4 g of a title compound was obtained as white solid.

$^1$H NMR (400 MHz, CDCl$_3$) δ 3.44 (s, 3H), 3.93 (s, 6H), 4.47 (s, 2H), 6.62 (s, 2H), 7.19 (s, 2H)

Production Example 14

N-Cyclopropylmethyl-2-ethyl-7-iodo-N-(tetrahydro-2H-pyran-4-ylmethyl)pyrazolo[1,5-a]pyridine-3-amine

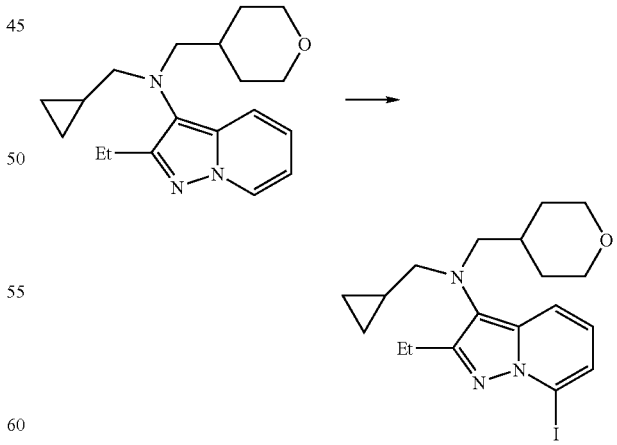

N-Cyclopropylmethyl-2-ethyl-N-(tetrahydro-2H-pyran-4-ylmethyl)pyrazolo[1,5-a]pyridine-3-amine (500 mg, 1.6 mmol) was dissolved in tetrahydrofuran (4.5 mL), and cooled in a dry ice-ethanol bath. Into the reaction mixture, a 1.6M n-butyllihium hexane solution (1.5 mL, 2.4 mmol) was dropped at −73 to −64.5° C. The reaction mixture was stirred for 1 hour, then, pentafluoroiodobenzene (706 mg, 2.4 mmol) was dropped, and the mixture was further stirred for 1 hour and 20 minutes. Then, to the reaction mixture was added iodine (406 mg, 1.6 mmol) and the mixture was stirred at room temperature. To the reaction mixture was added a sodium thiosulfate aqueous solution (20 mL) and heptane (15 mL).

The mixture of organic layer and aqueous layer was shaken sufficiently, and the organic layer was separated. The organic layer was further washed with water (10 mL), then, 5N hydrochloric acid (10 mL) was added, and the organic layer and aqueous layer were shaken sufficiently.

From the mixture, an organic layer and an aqueous layer were separated.

From the organic layer, the solvent was distilled off under reduced pressure, and pentafluoroiodobenzene was recovered. On the other hand, to the aqueous layer was added a 5N sodium hydroxide aqueous solution (9 mL) under cooling in a nice water bath, then, toluene (10 mL) was added, and the mixture of organic layer and aqueous layer was sufficiently shaken, and the organic layer was separated. The aqueous layer was extracted again by toluene (10 mL) added, both the organic layers were combined and concentrated, to obtain 632 mg of a title compound as deep green oil (yield: 90%).

Production Example 15

N-Cyclopropylmethyl-2-ethyl-7-iodo-N-(tetrahydro-2H-pyran-4-ylmethyl)pyrazolo[1,5-a]pyridine-3-amine

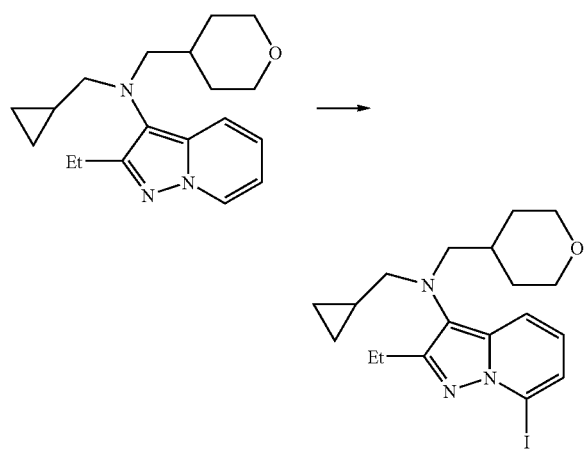

Under nitrogen flow, a solution of N-cyclopropylmethyl-2-ethyl-N-(tetrahydro-2H-pyran-4-ylmethyl)pyrazolo[1,5-a]pyridine-3-amine (1.27 g, 4.05 mmol) in tetrahydrofuran (11 mL) was cooled in a dry ice/ethanol bath. When the inner temperature of the reaction mixture reached −70° C., into the reaction mixture was dropped n-butyllithium (1.6M hexane solution; 3.85 mL, 6.08 mmol) over 8 minutes, and the mixture was stirred for 1 hour. Then, into the reaction mixture was dropped pentafluoroiodobenzene (1.62 mL, 12.15 mmol) over 10 minutes, and the mixture was stirred for 1 hour. Thereafter, into the reaction mixture was dropped mixed liquid of tetrahydrofuran (2 mL) and water (2 mL). To the reaction mixture was added water (25 mL) and heptane (25 mL), and an organic layer was separated. Then, the organic layer was washed with water (25 mL).

Then, to the organic layer was added 5N hydrochloric acid (13 mL) and an aqueous layer was separated. Then, into the aqueous layer was dropped a 5N-sodium hydroxide aqueous solution (13.5 mL), and t-butyl methyl ether (25 mL). From the mixture, an organic layer was separated and this organic layer was concentrated under reduced pressure. To the residue was added acetonitrile (6 mL) and water (6 mL), and further a seed crystal of a title compound. The mixture was stirred strongly overnight. A precipitate was filtrated, and the resultant precipitate was washed twice with mixed liquid (6 mL) of acetonitrile and water, and dried under reduced pressure, to obtain 1.17 g of a title compound as gray crystal (yield: 63%).

Production Example 16

N-Cyclopropylmethyl-2-ethyl-7-iodo-N-(tetrahydro-2H-pyran-4-ylmethyl)pyrazolo[1,5-a]pyridine-3-amine

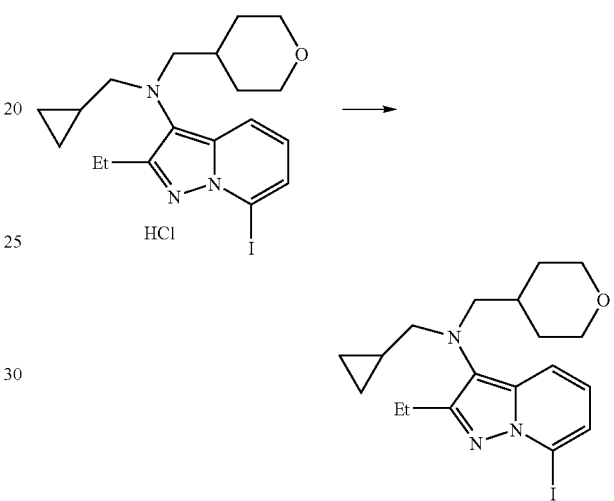

To N-cyclopropylmethyl-2-ethyl-7-iodo-N-(tetrahydro-2H-pyran-4-ylmethyl)pyrazolo[1,5-a]pyridine-3-amine hydrochloride (16 g) was added saturated sodium bicarbonate water (200 mL) to give neutrality. Then, ethyl acetate (100 mL) was added to this, and an organic layer was separated. From the organic layer, the solvent was distilled off under reduced pressure. Into the resulting residue was dropped acetonitrile (30 mL) and water (120 mL), the mixture was stirred overnight, and the resulting precipitate was filtrated. The precipitate was dried under reduced pressure, and 13 g of a title compound was obtained as white crystal.

Production Example 17

N-Cyclopropylmethyl-N-{7-[2,6-dimethoxy-4-(methoxymethyl)-phenyl]-2-ethylpyrazolo[1,5-a]pyridine-3-yl}-N-(tetrahydro-2H-4-pyranylmethyl)amine p-toluenesulfonate

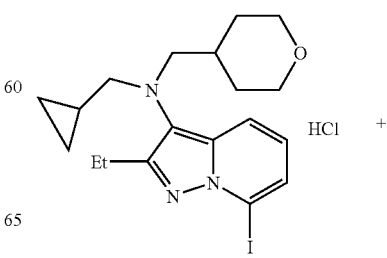

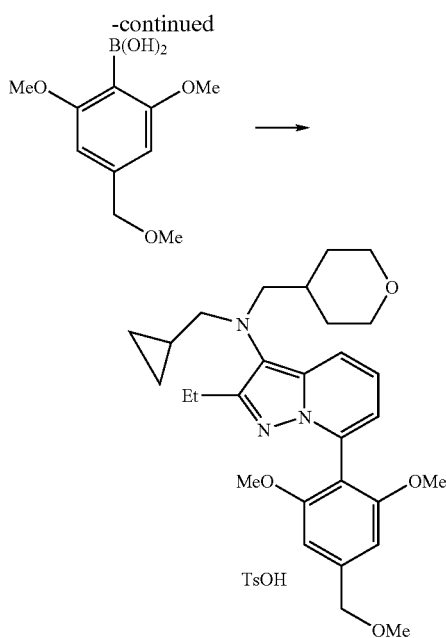

N-Cyclopropylmethyl-N-(2-ethyl-7-iodopyrazolo[1,5-a]pyridine-3-yl)-N-(tetrahydro-2H-4-pyranylmethyl)amine hydrochloride (193 g, 405 mmol), 2,6-dimethoxy-4-(methoxymethyl)phenylboric acid (143 g, 105 mmol, 1.56 equivalent), palladium acetate (4.7 g, 21 mmol, 5 mol %), triphenylphosphine (27.6 g, 105 mmol, 26 mol %), potassium carbonate (203 g, 1.47 mmol, 3.63 equivalent), dimethoxyethane (6667 mL) and water (3333 mL) were charged in a flask. Heating in an oil bath at 100° C. was initiated, and an atmosphere in the reaction system was purged with a nitrogen gas. About 6 hours after initiation of reflux, the reaction mixture was cooled to room temperature.

Thereafter, to the reaction mixture was added toluene (2000 mL), and a separated aqueous layer was removed. The toluene layer was extracted twice with 5N hydrochloric acid (first: 3000 mL, second: 1000 mL). Isopropyl acetate (2000 mL) was added to an aqueous layer, and under cooling in an ice water bath, a 5N sodium hydroxide aqueous solution (4200 mL) was added to give pH 14, and an isopropyl acetate layer was separated. The isopropyl acetate layer was washed with a 10% ethylenediamine aqueous solution (three times with 2000 mL) and water (twice with 2000 mL), and concentrated, then, ethanol (400 mL) was added. Azeotropic distillation was performed, and the reaction mixture was concentrated to obtain 207 g of green solid.

The residue was dissolved in ethanol (1720 mL) with heating, and a solution of p-toluenesulfonic acid mono-hydrate (65.5 g, 344 mmol) in ethanol (170 mL) was dropped at an inner temperature of 60° C. over a period of 3 minutes. Thereafter, the mixture was allowed to cool, and stirred. When the inner temperature reached 35° C., a seed crystal (100 mg) was added. After 30 minutes, the mixture was cooled in a thermostat control bath of 7° C., and stirred for 15 hours and 45 minutes. Thereafter, the precipitated crystal was filtrated, and washed with isopropanol (400 mL). The crystal was dried at 60° C. under reduced pressure for 3.5 hours, to obtain 214 g of a title compound as white crystal (yield: 79.5%).

What is claimed that:

1. A compound represented by following formula, or a hydrochloride or hydrobromide salt thereof, or a solvate of said hydrochloride or hydrobromide salt:

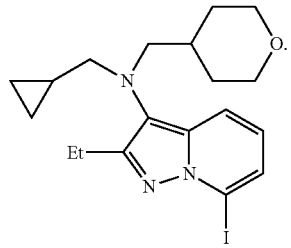

2. The salt according to claim 1, which is N-cyclopropylmethyl-N-(2-ethyl-7-iodopyrazolo[1,5-a]pyridine-3-yl)-N-(tetrahydro-2H-4-pyranylmethyl)amine hydrochloride.

3. A method for preparing a compound (II) represented by following formula:

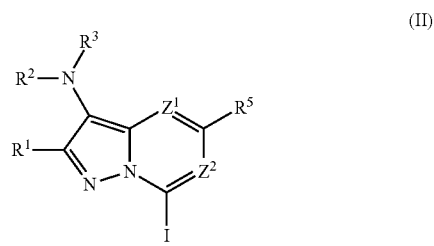

wherein
$Z^1$ and $Z^2$ each independently is a methine group;
$R^5$ is a hydrogen atom;
$R^1$ is an ethyl group;
$R^2$ is cyclopropylmethyl, and
$R^3$ is 4-pyranylmethyl,
or a hydrochloride or hydrobromide salt thereof, or a solvate of said hydrochloride or hydrobromide salt:
comprising the steps of:
reacting a compound (I) represented by following formula:

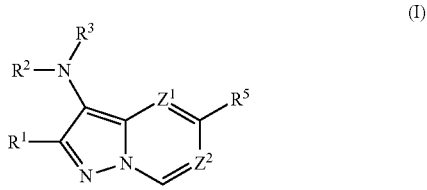

wherein $Z^1$, $Z^2$, $R^1$, $R^2$, $R^3$ and $R^5$ have the same definitions as described above for $Z^1$, $Z^2$, $R^1$, $R^2$, $R^3$ and $R^5$, respectively, with an organometallic reagent, and thereafter reacting the resulting product with pentafluoroiodobenzene, to produce the compound (II) or said salt thereof, or said solvate of said salt.

4. The method according to claim 3, wherein the organometallic reagent is n-butyllithium, t-butyllithium, sec-butyllithium, phenyllithium, lithiumdiisopropylamide, n-butylmagnesiumbromide or isopropylmagnesiumbromide.

5. The method according to claim 3, wherein iodine is added after reacting pentafluoroiodobenzene.

* * * * *